(12) United States Patent
Truong

(10) Patent No.: US 11,566,736 B2
(45) Date of Patent: Jan. 31, 2023

(54) ASEPTIC FLUID COUPLINGS

(71) Applicant: Colder Products Company, Roseville, CA (US)

(72) Inventor: Loi T. Truong, Savage, MN (US)

(73) Assignee: Colder Products Company, Roseville, MN (US)

( * ) Notice: Subject to any disclaimer, the term of this patent is extended or adjusted under 35 U.S.C. 154(b) by 196 days.

(21) Appl. No.: 17/138,020

(22) Filed: Dec. 30, 2020

(65) Prior Publication Data

US 2021/0199220 A1    Jul. 1, 2021

Related U.S. Application Data

(60) Provisional application No. 62/955,795, filed on Dec. 31, 2019.

(51) Int. Cl.
*F16L 37/084*    (2006.01)

(52) U.S. Cl.
CPC ....... *F16L 37/0841* (2013.01); *F16L 2201/20* (2013.01)

(58) Field of Classification Search
CPC . F16L 37/0841; F16L 2201/20; F16L 37/248; F16L 2201/44; A61M 39/165; A61M 39/39; A61M 39/26; F16K 35/02; Y10T 137/87957
USPC .............................................. 137/384; 285/4
See application file for complete search history.

(56) References Cited

U.S. PATENT DOCUMENTS

| | | | |
|---|---|---|---|
| 1,871,370 A * | 8/1932 | Jacques | F16L 37/248 285/361 |
| 2,919,914 A * | 1/1960 | Harless | B65H 45/161 493/431 |
| 4,334,551 A | 6/1982 | Pfister | |
| 4,429,713 A | 2/1984 | Walter | |
| 4,664,148 A | 5/1987 | Magnuson | |
| 4,804,015 A | 2/1989 | Albinsson | |
| 5,806,564 A | 9/1998 | Wilcox | |
| 5,971,019 A | 10/1999 | Imal | |
| 6,024,124 A | 2/2000 | Braun et al. | |
| 6,161,578 A | 12/2000 | Braun et al. | |
| 6,237,631 B1 | 5/2001 | Giesler et al. | |
| 7,469,472 B2 | 12/2008 | deCler et al. | |

(Continued)

FOREIGN PATENT DOCUMENTS

| | | |
|---|---|---|
| EP | 0028601 | 5/1981 |
| WO | WO 1980/001507 | 7/1980 |

(Continued)

OTHER PUBLICATIONS

International Preliminary Report on Patentability in International Application No. PCT/US2020/067487, dated Jul. 14, 2022, 8 pages.

(Continued)

*Primary Examiner* — Michael R Reid
(74) *Attorney, Agent, or Firm* — Fish & Richardson P.C.

(57) ABSTRACT

Some fluid coupling devices described herein are configured for use in fluid systems for purposes of providing a single-use, aseptic disconnection functionality that substantially prevents fluid spillage when being disconnected. In some embodiments, the coupling portions cannot be reconnected to each other after being disconnected from each other.

20 Claims, 15 Drawing Sheets

(56) References Cited

U.S. PATENT DOCUMENTS

| | | |
|---|---|---|
| 7,547,047 B2 | 6/2009 | deCler et al. |
| 7,959,192 B2 | 6/2011 | Elton et al. |
| 8,690,120 B2 | 4/2014 | Hartnett et al. |
| 2007/0025811 A1 | 3/2007 | Wilhelm |
| 2007/0073215 A1 | 3/2007 | Wieslander |
| 2008/0185056 A1 | 8/2008 | Diodati et al. |
| 2009/0051161 A1 | 2/2009 | Eskstrom |
| 2009/0076434 A1 | 3/2009 | Mischelevich |
| 2010/0230950 A1 | 9/2010 | Scott et al. |
| 2011/0240158 A1 | 10/2011 | Py |
| 2012/0031515 A1 | 2/2012 | Whitaker |
| 2013/0341904 A1 | 12/2013 | Lehmann et al. |
| 2014/0345748 A1 | 11/2014 | Rogers et al. |
| 2016/0158519 A1 | 6/2016 | Rhinehart |
| 2018/0296817 A1 | 10/2018 | Burdge et al. |
| 2019/0298985 A1 | 10/2019 | Truong |

FOREIGN PATENT DOCUMENTS

| | | |
|---|---|---|
| WO | WO 2008/094707 | 8/2008 |
| WO | WO 2012/114105 | 8/2012 |
| WO | WO 2014/160756 | 10/2014 |
| WO | WO 2017/062859 | 4/2017 |

OTHER PUBLICATIONS

European Extended Search Report in European Application No. EP 16783779, dated Oct. 31, 2018, 9 pages.

European Extended Search Report in European Application No. EP16854486, dated May 20, 2019, 7 pages.

International Preliminary Report on Patentability in International Application No. PCT/US2016/028467, dated Oct. 24, 2017 9 pages.

International Preliminary Report on Patentability in International Application No. PCT/US2016/056120, dated Apr. 10, 2018, 10 pages.

International Search Report and Written Opinion in International Application No. PCT/US2016/028467, dated Jul. 26, 2016, 9 pages.

International Search Report and Written Opinion in International Application No. PCT/US2016/056120, dated Dec. 13, 2016, 18 pages.

Invitation to Pay Additional Fees in International Application No. PCT/US20/67487, dated Mar. 3, 2021, 2 pages.

International Search Report and Written Opinion in International Application No. PCT/US2020/67487, dated May 3, 2021, 11 pages.

\* cited by examiner

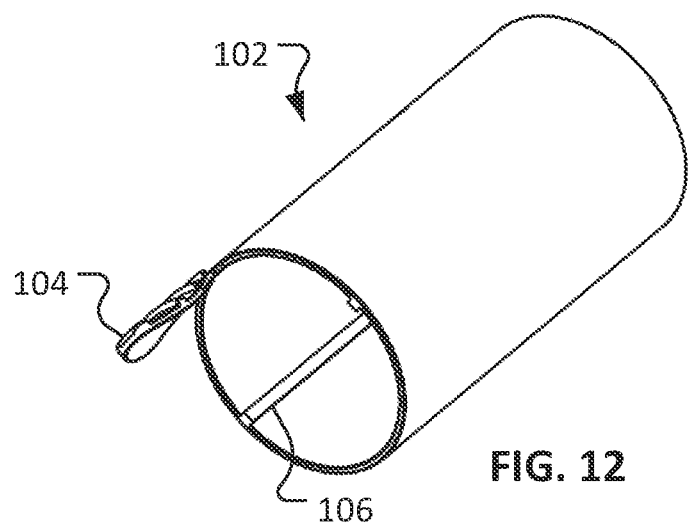
FIG. 12
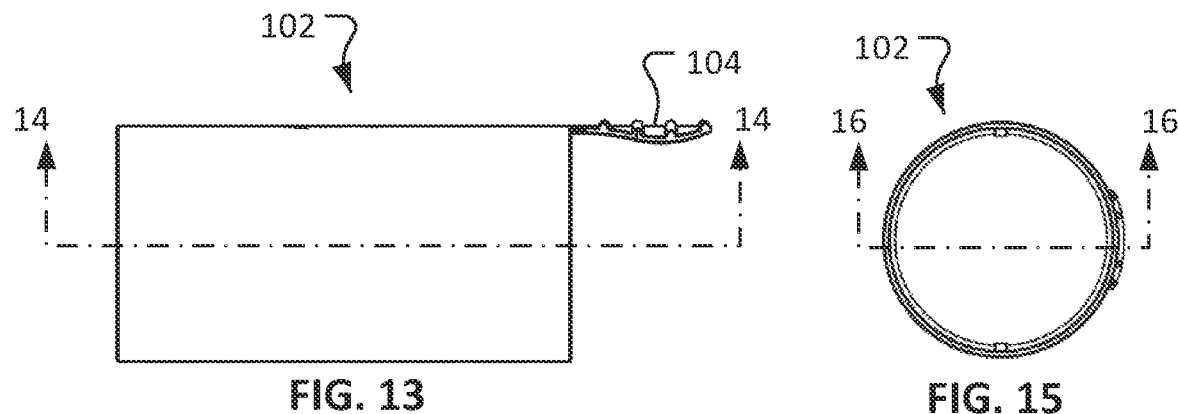
FIG. 13
FIG. 15
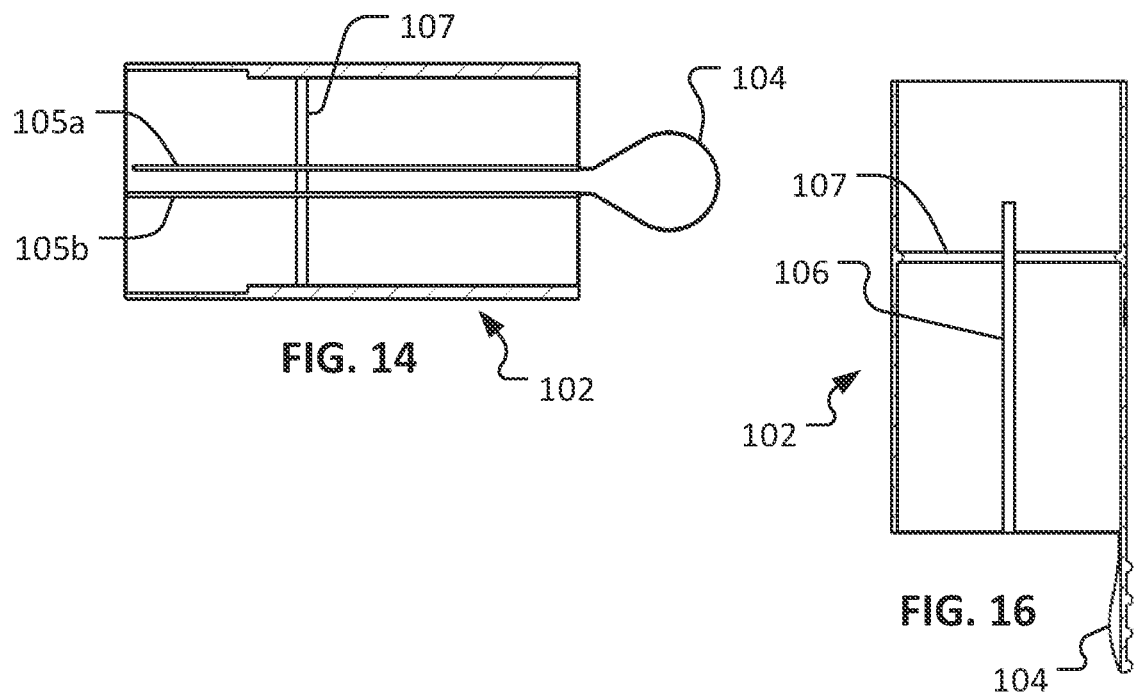
FIG. 14
FIG. 16

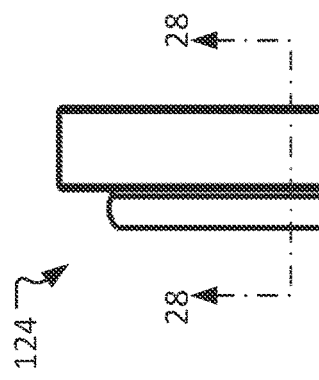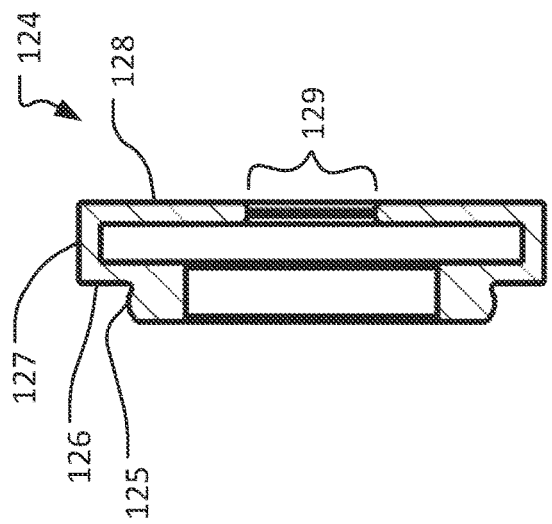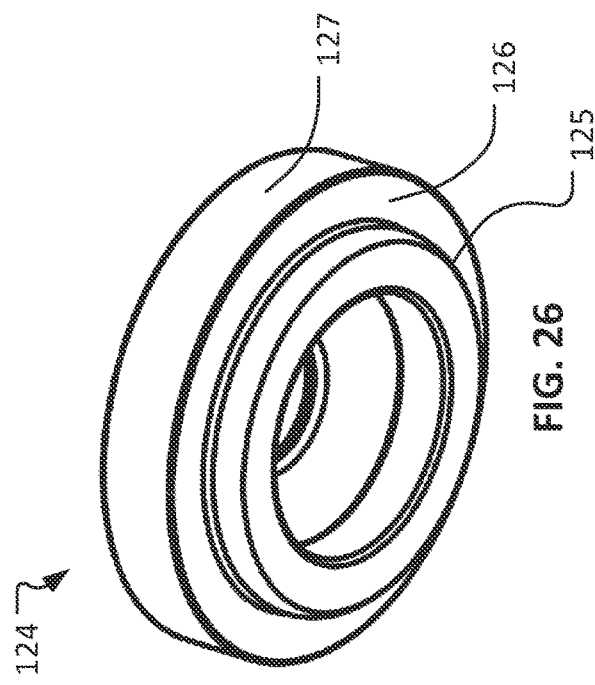

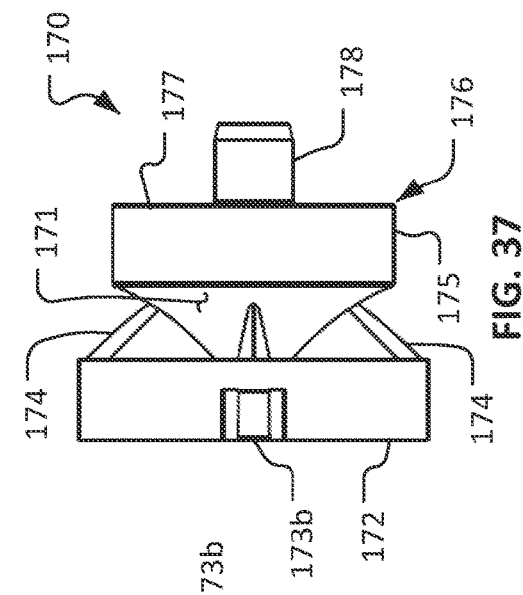
FIG. 36
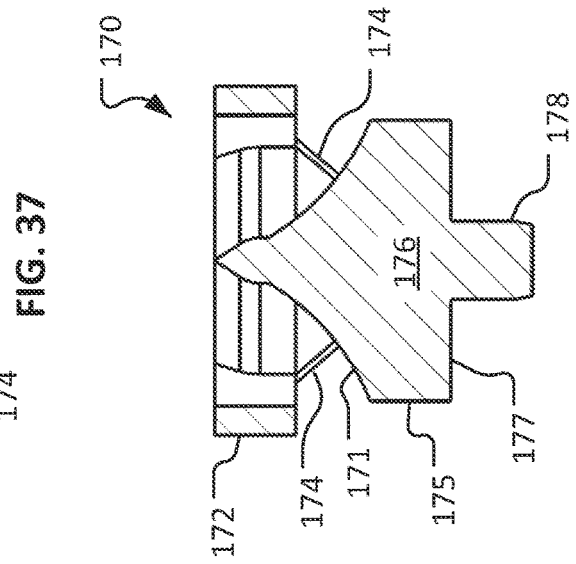
FIG. 37
FIG. 38
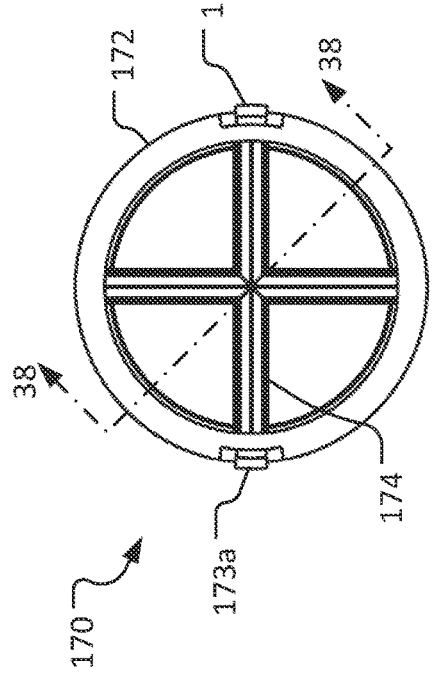
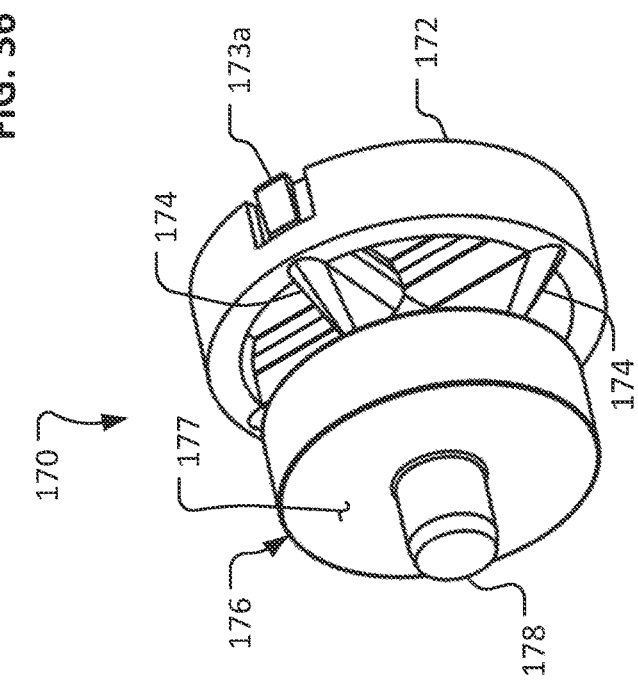
FIG. 35

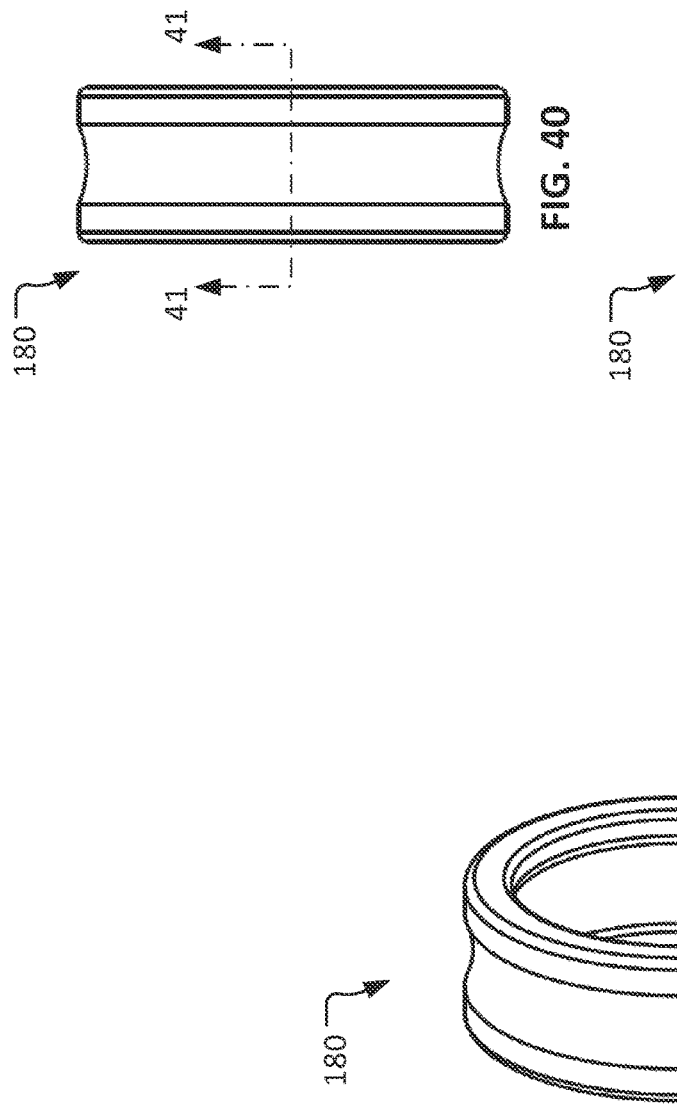

ASEPTIC FLUID COUPLINGS

CROSS-REFERENCE TO RELATED APPLICATIONS

This application claims the benefit of U.S. Provisional Application Ser. No. 62/955,795, filed Dec. 31, 2019. The disclosure of the prior application is considered part of (and is incorporated by reference in) the disclosure of this application.

BACKGROUND

1. Technical Field

This document relates to fluid coupling devices for fluid systems and methods. For example, some embodiments described in this document relate to single-use, aseptic disconnection fluid coupling devices.

2. Background Information

Fluid systems commonly include components such as tubing, pumps, reservoirs, fittings, couplings, heat exchangers, sensors, filters, valves, seals, and the like. Such components can be connected together in a network to define one or more fluid flow paths. Some fluid systems are open systems, meaning that the fluid flows through the network once and then exits the network. Other fluid systems are closed systems, meaning that the fluid recirculates within the network of components. Fluids may be moved through fluid systems using fluid pressure differentials. For example, in some cases, a pump or a vacuum source is used to create a pressure differential that causes the fluid to flow within the fluid system. In another example, gravity is used to cause the fluid to flow within the fluid system. In other examples, a combination of such techniques is used to cause the fluid to flow within the fluid system.

In the context of some fluid systems, such as some bioprocessing fluid systems, it may be desirable to have a tube coupler that can aseptically disconnect a fluid flow path. In one such example implementation, it is desirable to disconnect aseptically one or more media bags from a bioreactor system. In that scenario, an aseptic coupling can be used to disconnect the media bag(s) from the bioreactor system while substantially preventing biological contamination of the media bags and of the bioreactor via the disconnected ends of the coupling during and after the disconnection process. Such an aseptic coupling will also serve to limit the exposure of the fluid to the surrounding environment.

SUMMARY

This document describes fluid coupling devices for fluid systems and methods. In some embodiments, the fluid coupling devices can be implemented as single-use, aseptic disconnection fluid coupling devices that are configured to reduce the likelihood of fluid spillage when being disconnected. In some embodiments, the coupling portions cannot be reconnected to each other after being disconnected from each other. Accordingly, the fluid coupling devices are called "single-use" disconnect couplings. In the context of this disclosure, the term "fluid" includes gases, liquids, and powders.

In particular embodiments, the fluid coupling devices described herein are single-use devices because, after the two portions of the coupling (also referred to herein as "coupling halves" and/or "connectors") are disconnected from each other, the fluid paths of one or both portions are irreversibly blocked and the coupling portions cannot even be mechanically coupled together again. Hence, in these particular embodiments, the fluid coupling devices provided herein are structurally configured to be single-use disconnection devices so that, after the single-use coupling halves have been disconnected from each other, they cannot be operably reconnected to each other (or to any other coupling halves).

Additionally, in such single-use embodiments or in other embodiments, the fluid coupling devices can be configured as "aseptic" coupling devices in that, during disconnection and after the two portions of the coupling device are disconnected from each other, the fluid paths of both portions are mechanically blocked, e.g., by a valve, so as to inhibit biological contamination migrating into the flow paths. Such an "aseptic" coupling will also serve to limit the exposure of the fluid to the surrounding environment.

Further, in such single-use embodiments, or other embodiments, the fluid coupling devices can be configured as no-spill coupling devices because, as the two portions of the coupling device are being disconnected from each other, one or more mechanical components will reduce the likelihood of fluid discharge out of the fluid system (for example, by blocking as such discharge paths) and by preventing spillage from fluid inclusion.

In one aspect, this disclosure is directed to a fluid coupling device. For example, this disclosure is directed to a single-use aseptic fluid coupling device. In some embodiments, such a single-use aseptic fluid coupling device includes a male coupling and a female coupling that are releasably coupled together. The male coupling includes a male housing defining an internal space and a longitudinal axis. A male coupling valve member is disposed within the internal space and slidable relative to the male housing along the longitudinal axis of the male housing from an open position to a closed position. The female coupling includes a female housing defining an internal space and a longitudinal axis. A stem is fixedly coupled to the female housing and extending along the longitudinal axis of the female housing. The stem has a front surface facing the male coupling valve member. The stem defines an open bore extending longitudinally and one or more lateral openings fluidly coupling the open bore and the internal space of the male housing such that an open flow path extends through the female coupling and the male coupling while they are releasably coupled to each other. The female coupling also includes an elastomeric seal disposed on the front surface of the stem such that the male coupling valve member is abutting the elastomeric seal.

Such a single-use aseptic fluid coupling device may optionally include one or more of the following features. The front surface of the stem may be planar. The front surface of the stem may define an opening. The male coupling valve member may include a projection that extends through the elastomeric seal and the opening. In some embodiments, a spring in the internal space of the male housing moves the male coupling valve member to the closed position in response to uncoupling the male and female couplings from each other. The male coupling valve member may lock in the closed position in response to moving to the closed position. The single-use aseptic fluid coupling device may also include a tear-away sleeve coupled to the male and female couplings while the male and female couplings are releasably coupled to each other. In some embodiments, the tear-away sleeve prevents uncoupling of the male and female couplings while the tear-away sleeve is coupled to the male and female couplings. In particular embodiments, in order to uncouple the male and female couplings from each other, the tear-away sleeve must be destructively removed from being coupled to the male and female couplings. In some embodiments, the male and female couplings can be uncoupled from each other by simultaneously rotating and translating the male coupling relative to the female coupling. In certain embodiments, after the male and female couplings have been uncoupled from each other, latches are activated that block and prevent the male and female couplings from being coupled together again.

In another aspect, this disclosure is directed to another embodiment of a single-use aseptic fluid coupling device. Such a single-use aseptic fluid coupling device includes a male coupling and a female coupling that are releasably coupled together. The male coupling includes a male housing defining an internal space and a longitudinal axis. The male coupling also includes a male coupling valve member within the internal space. The male coupling valve member is slidable relative to the male housing along the longitudinal axis of the male housing from an open position to a closed position. The female coupling includes a female housing defining an internal space and a longitudinal axis. The female coupling also includes a stem fixedly coupled to the female housing and extending along the longitudinal axis of the female housing. The stem defines an open bore extending longitudinally and one or more lateral openings fluidly coupling the open bore and the internal space of the male housing such that an open flow path extends through the female coupling and the male coupling while they are releasably coupled to each other. Uncoupling the male and female couplings from each other, activates one or more latches that block and prevent the male and female couplings from being coupled together again.

Such a single-use aseptic fluid coupling device may optionally include one or more of the following features. The one or more latches may include a flexible arm that is biased to seek a position in which it blocks a projection extending radially from one of the male housing or the female housing from entering a corresponding slot defined by the other one of the male housing or the female housing, thereby preventing the male and female couplings from being coupled together again. In some embodiments, a spring in the internal space of the male housing moves the male coupling valve member to the closed position in response to uncoupling the male and female couplings from each other. The male coupling valve member may lock in the closed position in response to moving to the closed position. The single-use aseptic fluid coupling device may also include a tear-away sleeve coupled to the male and female couplings while the male and female couplings are releasably coupled to each other. In some embodiments, the tear-away sleeve prevents uncoupling of the male and female couplings while the tear-away sleeve is coupled to the male and female couplings. In particular embodiments, in order to uncouple the male and female couplings from each other, the tear-away sleeve must be destructively removed from being coupled to the male and female couplings. In certain embodiments, the male and female couplings can be uncoupled from each other by simultaneously rotating and translating the male coupling relative to the female coupling. The female coupling may also include an elastomeric seal disposed on a front face surface of the stem such that the male coupling valve member is abutting the elastomeric seal. The front face surface of the stem may be planar and define an opening. The male coupling valve member may include a projection that extends through the elastomeric seal and the opening.

Particular embodiments of the subject matter described in this document can be implemented to realize one or more of the following advantages. First, in some embodiments the fluid coupling devices provided herein are configured to be used with tubing that is relatively large (e.g., diameters of ¼ inch and larger).

Second, in some embodiments, the fluid coupling devices may advantageously provide a user with audible and/or tactile feedback in reference to the motions performed for physically disconnecting the two portions of the fluid coupling devices from each other. Such audible and/or tactile feedback can provide the user with an efficient and conclusive indication or confirmation of the proper function and desired configuration of the fluid coupling device.

Third, some embodiments of the fluid coupling devices provide an improved non-spill aseptic disconnection capability that may optionally reduce or eliminate the need for sterile rooms or sterile benchtop environments in some cases. As such, these embodiments of the aseptic fluid coupling devices described herein may facilitate efficient and cost-effective operations or uses that would otherwise be high-cost or even cost prohibitive in some traditional settings that required the disconnection of particular fluid couplings in a sterile room or within a sterile flow-hood to prevent biological contamination.

Fourth, some embodiments of the fluid coupling devices provided herein are advantageously designed with a robust locking system. That is, when the two halves of the coupling are operably connected with each other to provide a fluid flow path therethrough, they are also mechanically locked together. In some embodiments, to release the lock, a tear-away sleeve must be removed first. This redundant requirement (e.g., removal of the tear-away sleeve and subsequent mechanically uncoupling the halves of the coupling) for unlocking the coupling halves may reduce the likelihood of unintentional disconnections.

Fifth, in some optional embodiments, when the two halves of the fluid coupling devices are mated together, most components of the coupling device are not under substantial mechanical stress that would induce warping. This configuration is advantageous because, for example, the heat associated with some sterilization processes may cause stressed components to warp or to induce warping of other components. Since most of the components of the coupling device are not under substantial mechanical stress during sterilization, the propensity for the coupling device to warp is reduced or substantially eliminated.

Sixth, in some embodiments, the coupling halves of the fluid coupling devices provided herein are designed so that the uncoupling process involves closing valves in a particular sequence so that spillage related to fluid inclusion is eliminated or minimized.

Unless otherwise defined, all technical and scientific terms used herein have the same meaning as commonly understood by one of ordinary skill in the art to which this disclosure pertains. In addition, the materials, methods, and examples of the embodiments described herein are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIGS. 12-16 show various views of a tear-away sleeve component of the fluid coupling device of FIG. 1.

FIG. 26 is a perspective view of a multi-functional seal component that couples to the stem of FIG. 24.

FIG. 27 is a side view of the seal of FIG. 26.

FIG. 28 is a longitudinal cross-sectional view of the seal of FIG. 26 taken along the break line 28-28.

FIGS. 35-38 are various views of a valve component of the male coupling portion of FIG. 32.

FIGS. 39-41 are various views of a seal component of the male coupling portion of FIG. 32.

Like reference numbers represent corresponding parts throughout.

DETAILED DESCRIPTION OF ILLUSTRATIVE EMBODIMENTS

Figure 1:
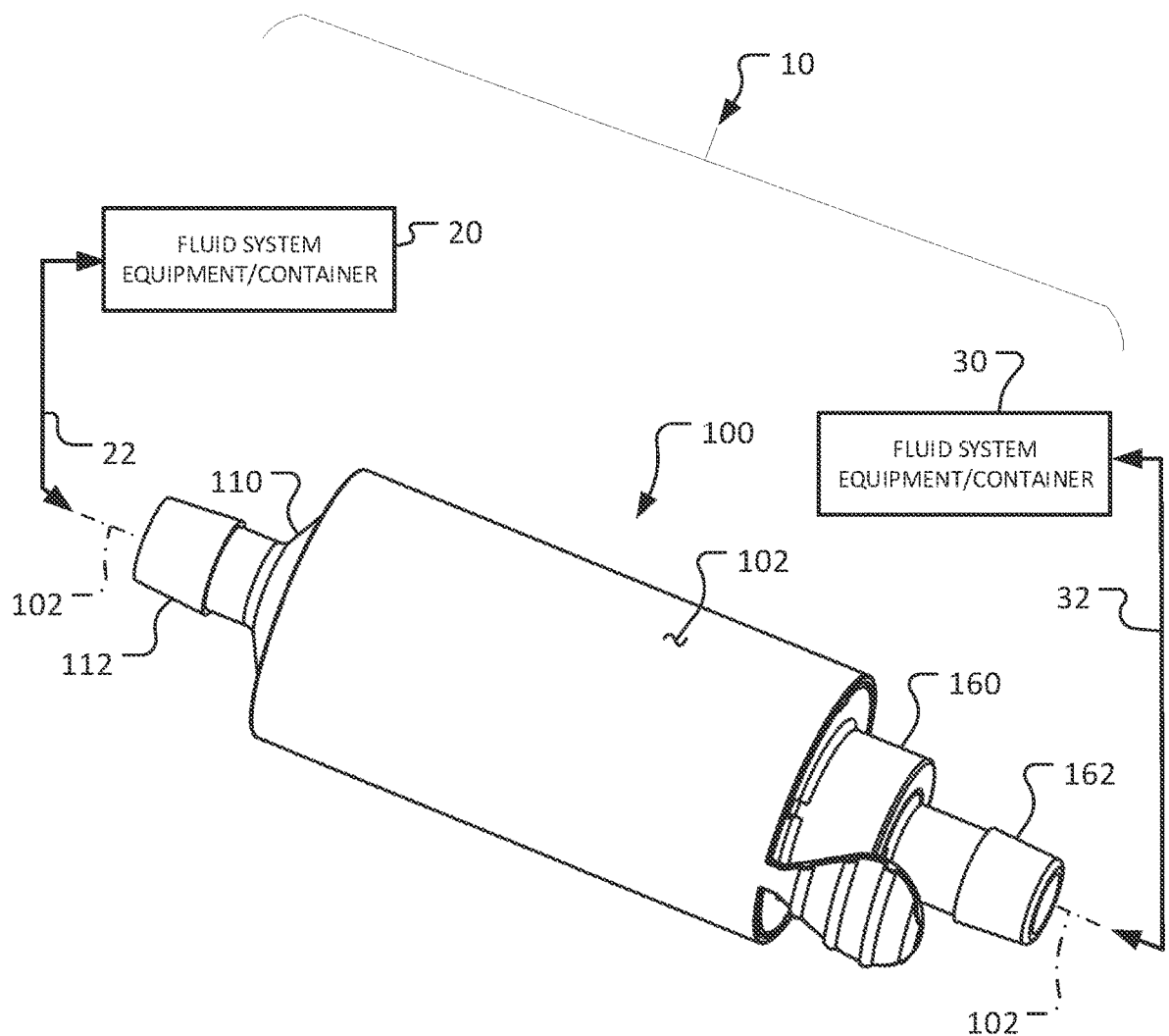
FIG. 1 is a perspective view of an example fluid system including an example fluid coupling device arranged in an operative connected configuration, in accordance with some embodiments provided herein.

Referring to FIG. 1, some example embodiments of a fluid system 10 include one or more example fluid coupling devices 100 configured to, for example, releasably connect a first fluid system equipment or container 20 to a second fluid system equipment or container 30. In some implementations, the fluid system 10 may include at least one fluid coupling device 100 that is a single-use, aseptic disconnection fluid coupling device, in which first and second mating components 110 and 160 are configured to disconnect from one another in a manner that provides an aseptic disconnection and that mechanically prevents reconnection and reuse of the fluid path through the mating components 110 and 160. (The first and second mating portions 110 and 160 are sometimes referred to herein as "coupling halves" or a "coupling-half" even though the components 110 and 160 are not necessarily equal halves in terms of size, shape, or weight.)

In one non-limiting example, the fluid coupling 100 can provide a single-use, aseptic disconnection capability for a fluid path between the fluid system equipment 20 in the form of a bioreactor system (connected directly to the coupling device 100 or connected via a fluid tube 22) and the fluid system container 30 in the form of a media bag (connected directly to the coupling device 100 or connected via a fluid tube 32).

Figure 2:
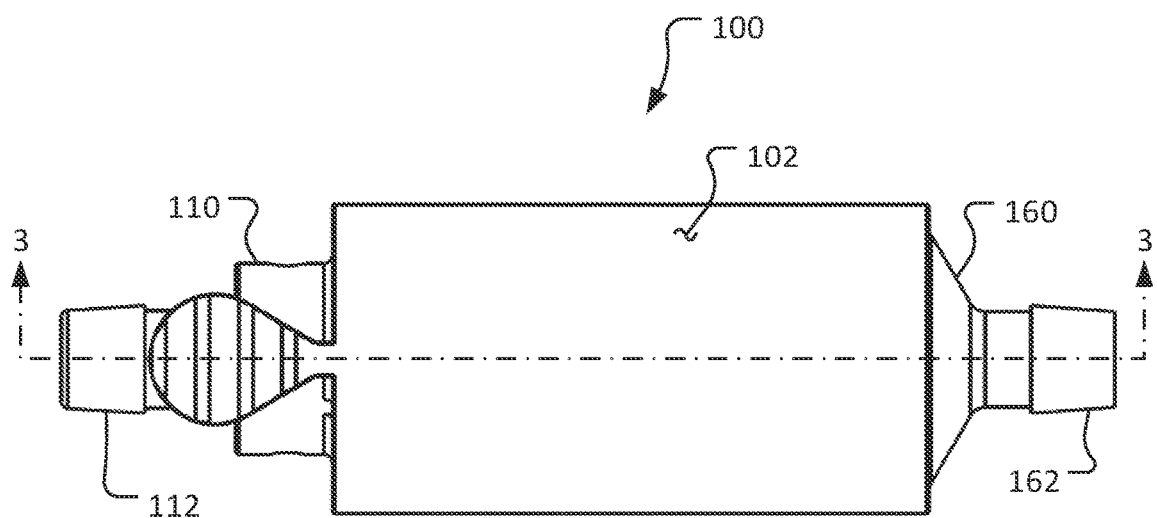
FIG. 2 is a side view of the fluid coupling device of FIG. 1 arranged in the operative connected configuration.

Generally, the coupling 100 is provided to an end user in the coupled arrangement, and with a tamper-proof tear-away sleeve 102 surrounding the coupled mating components 110 and 160, as depicted in FIGS. 1 and 2. In some cases, the coupling 100 is sterile or made to be sterilized. Each coupling-half 110 and 160, as well as the assembled coupling 100 overall, defines a longitudinal axis 102.

Still referring to FIGS. 1 and 2, the fluid coupling 100 in the depicted embodiment includes the tear-away sleeve 102 and the mating components 110 and 160 in the form of a female coupling 110 (or body 110) and a male coupling 160 (or insert 160). The female coupling 110 and the male coupling 160 are releasably coupled to each other. The coupling halves 110 and 160 are shown fully coupled (connected) in FIGS. 1 and 2, such that an open flow path is provided through the fluid coupling 100. That is, in the fully coupled, operable configuration as shown, fluid can flow through the coupling 100 between a first connection 112 and a second connection 162.

While the first and second connections 112 and 162 are depicted as barbed connections, it should be understood that the coupling halves 110 and 160 can have any type of connections such as, but not limited to, threaded connections, elbows, tees, sanitary fittings, compression fittings, and the like, and combinations thereof.

The materials from which one or more of the components of the fluid coupling 100 are made of include thermoplastics or thermosets. In particular embodiments, the materials from which the components of the fluid coupling 100 are made of are thermoplastics, such as, but not limited to, acetal, polycarbonate, polysulfone, polyether ether ketone, polysulphide, polyester, polyvinylidene fluoride (PVDF), polyethylene, polyphenylsulfone (PPSU; e.g., Rader), polyetherimide (PEI; e.g., Ultem®), polypropylene, polyphenylene, polyaryletherketone, and the like, and combinations thereof. In some embodiments, the materials from which one or more of the components of the fluid coupling 100 are made of include metals such as, but not limited to stainless steel, brass, aluminum, plated steel, and the like. In particular embodiments, one or both of the coupling halves 110 and 160 is/are metallic-free. In some embodiments, one or both of the coupling halves 110 and/or 160 includes one or more plastic or metallic spring members (e.g., spring steel, stainless steel, and the like). In certain embodiments, fluid coupling 100 includes one or more gaskets or seals that are made of materials such as, but not limited to, silicone, fluoroelastomers (FKM), ethylene propylene diene monomer (EPDM), thermoplastic elastomers (TPE), buna, buna-N, thermoplastic vulcanizates (TPV), and the like.

Figure 10:
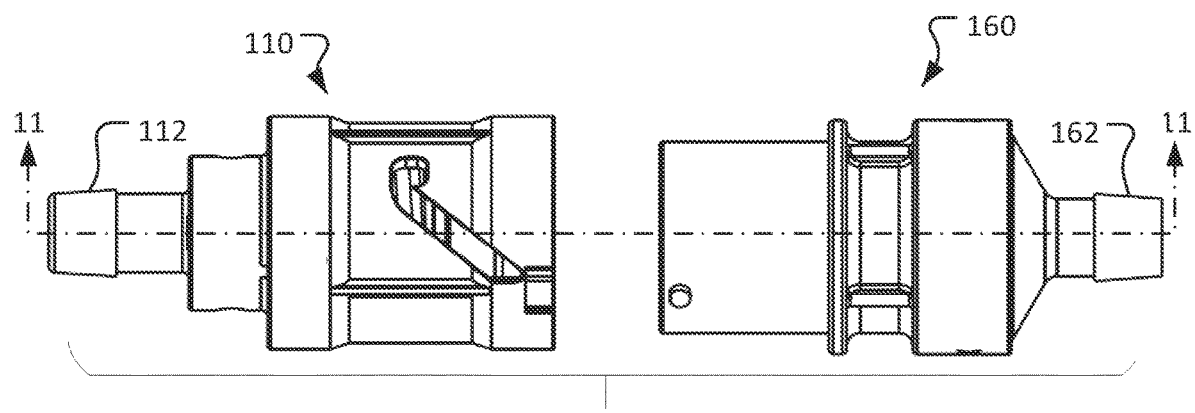
FIG. 10 is a side view of the fluid coupling device of FIG. 1 with the tear-away sleeve removed and the coupling halves in a state of disconnection.

The coupling halves 110 and 160 are shown fully uncoupled (disconnected) from each other in FIG. 10. In the fully uncoupled state, valves in each of the coupling halves 110 and 160 close to prevent fluid flow (as described further below).

Figure 3:
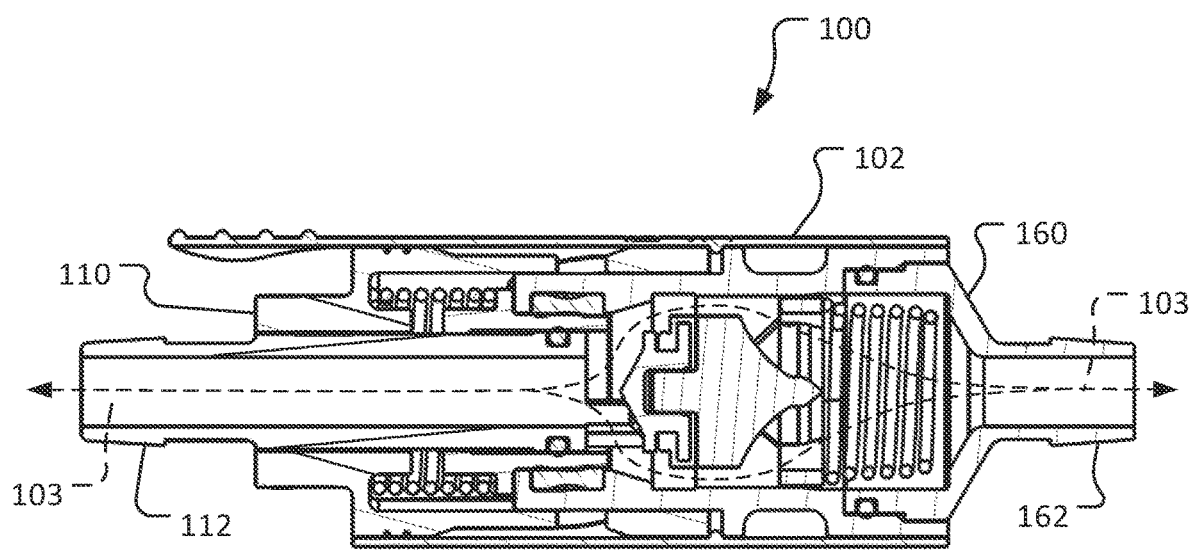
FIG. 3 is a longitudinal cross-sectional view of the fluid coupling device of FIG. 2 taken along the break line 3-3.

As shown in FIG. 3, an open flow path 103 exists through the fluid coupling 100 while the female coupling 110 and the male coupling 160 are operatively fully coupled together. In order to get a better understanding of what portions of the fluid coupling 100 constitute the female coupling 110, please refer to FIGS. 17 and 18 which show the female coupling 110 in isolation. In order to get a better understanding of what portions of the fluid coupling 100 constitute the male coupling 160, please refer to FIGS. 32-34 which show the male coupling 160 in isolation.

While the fluid coupling 100 is in its fully coupled, operable configuration, the tear-away sleeve 102 locks the coupling halves 110 and 160 in their respective operable positions. Therefore, to begin the procedure to disconnect the coupling halves 110 and 160 from each other, the user is first required to remove the tear-away sleeve 102.

The tear-away sleeve 102 is shown in isolation in FIGS. 12-16. It should be understood that the depicted tear-away sleeve 102 is merely one example of a type of a component that must be removed prior to uncoupling the coupling halves 110 and 160. It provides, in effect, a tamper-resistant feature to the fluid coupling 100.

In this embodiment, the tear-away sleeve 102 is a plastic (e.g., polypropylene, etc.) cylinder that includes a grip tab 104 extending from the cylinder. The grip tab 104 can be grasped by a user and then pulled (e.g., generally transversely, or in line with axis 102) to destructively remove the tear-away sleeve 102 from the coupling halves 110 and 160.

In the depicted embodiment, the grip tab 104 is aligned with a first thin-wall portion 105a and a second thin-wall portion 105b (FIG. 14). The wall thicknesses of the portions 105a-b are thinned so that the wall of the tear-away sleeve 102 will tend to tear apart along the portions 105a-b as the user pulls on the grip tab 104. In some embodiments, one of the thin-wall portions 105a-b extends all the way along the entire length of the tear-away sleeve 102 while the other thin-wall portion 105a-b stops short of extending the entire length. Accordingly, the strip between the thin-wall portions 105a-b made by the user's tearing action will conveniently stay attached to the tear-away sleeve 102, rather than becoming separated therefrom. Thereafter, the ripped tear-away sleeve 102 can be manually dislodged off from the coupling halves 110 and 160.

In some embodiments, the tear-away sleeve 102 includes one or more physical features that mechanically engage the tear-away sleeve 102 relative to the coupling halves 110 and 160. For example, in the depicted embodiment the tear-away sleeve 102 includes at least one longitudinal rib 106 and a circumferential rib 107. The ribs 106 and 107 project from the inner diameter of the tear-away sleeve 102 and engage in corresponding grooves defined by the coupling halves 110 and 160. The longitudinal rib(s) 106, for example, serve to inhibit relative rotation between the coupling halves 110 and 160 because the longitudinal rib(s) 106 extend within aligned grooves defined by each of the coupling halves 110 and 160. The circumferential rib 107, for example, can serve to lock the tear-away sleeve 102 to the coupling halves 110 and 160 by preventing the tear-away sleeve 102 from being longitudinally slidable relative to the coupling halves 110 and 160.

Figure 4:
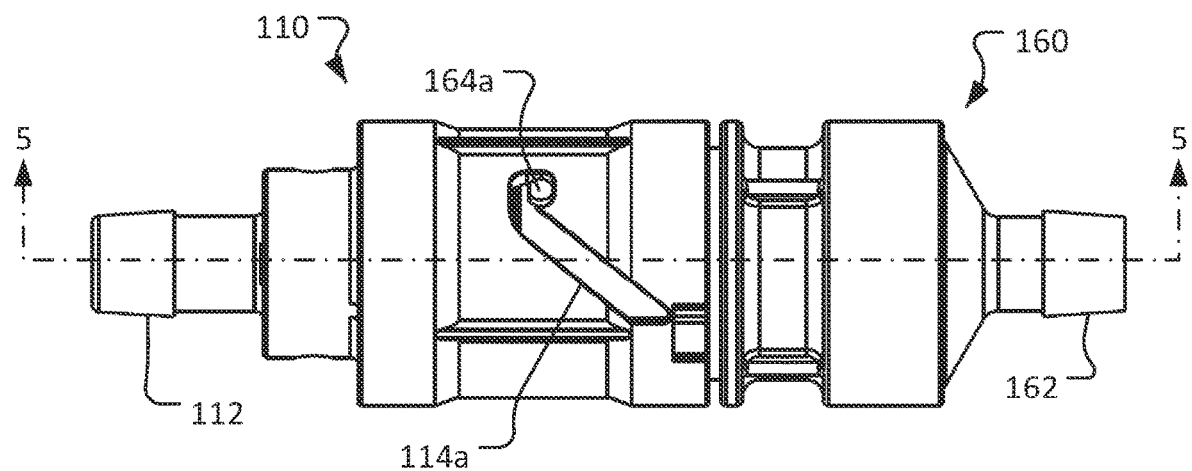
FIG. 4 is a side view of the fluid coupling device of FIG. 1 arranged in the operative connected configuration with the tear-away sleeve removed.
Figure 5:
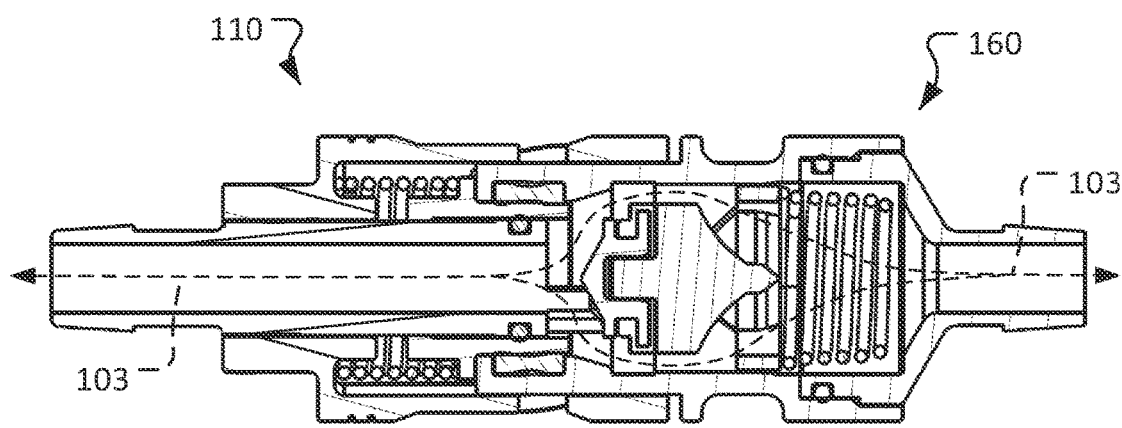
FIG. 5 is a longitudinal cross-sectional view of the fluid coupling device of FIG. 4 taken along the break line 5-5.

FIGS. 4 and 5 show the fluid coupling halves 110 and 160, after removal of the tear-away sleeve 102. This would be the state of the fluid coupling 100 in preparation for uncoupling the fluid coupling halves 110 and 160 from each other. Note that the open flow path 103 still exists in this configuration. That is, the valves of each of the fluid coupling halves 110 and 160 are open in this configuration, which is fully coupled.

While each of the fluid coupling halves 110 and 160 includes a spring that is compressed in the coupled configuration as shown, the forces from the springs are not able to longitudinally separate the fluid coupling halves 110 and 160 because of a latched engagement between the fluid coupling halves 110 and 160. In particular, the fluid coupling halves 110 and 160 are latched together by virtue of a pair of projections 164a-b (e.g., FIGS. 32 and 33) of the male coupling 160 that are engaged in a pair of slots 114a-b (e.g., FIGS. 17, 21, and 22) defined by the female coupling 110. The slots 114a-b, the majority of which extend helically, each include an end-of-travel detent position in which the projections 164a-b steadfastly reside while the fluid coupling 100 is in the fully coupled, operative configuration.

To begin separating the fluid coupling halves 110 and 160 from each other, the user grasps each one of the fluid coupling halves 110 and 160 and then pushes them longitudinally toward each other while simultaneously twisting them relative to each other. Those actions will unseat the projections 164a-b from the end-of-travel detent positions of the slots 114a-b. Once the projections 164a-b are unseated from the end-of-travel detent positions of the slots 114a-b, then user can then further rotate and simultaneously longitudinally translate the fluid coupling halves 110 and 160 away from each other so that the projections 164a-b travel along the slots 114a-b.

Figure 6:
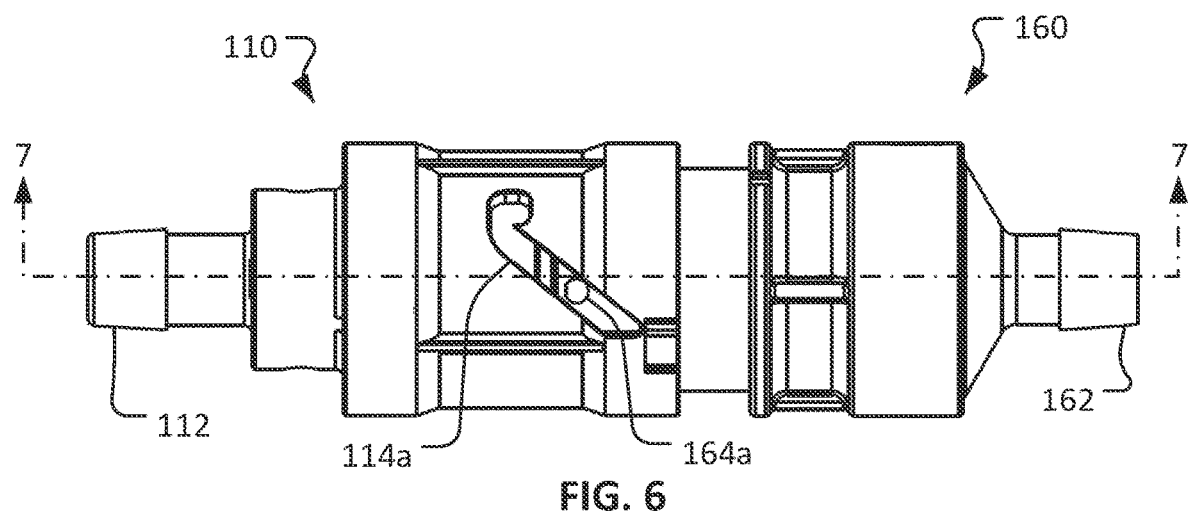
FIG. 6 is a side view of the fluid coupling device of FIG. 1 with the tear-away sleeve removed and configured in a first interim state during disconnection.
Figure 7:
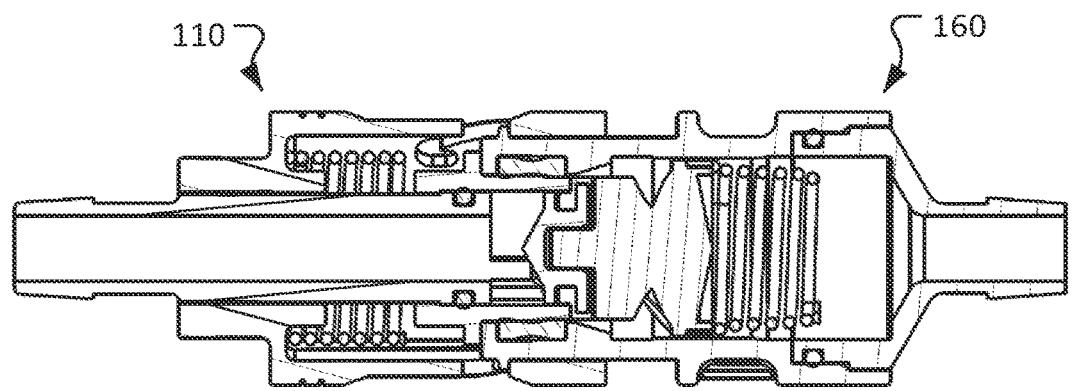
FIG. 7 is a longitudinal cross-sectional view of the fluid coupling device of FIG. 6 taken along the break line 7-7.

FIGS. 6 and 7 depict the fluid coupling halves 110 and 160 in a first state of partial disengagement from each other. This relative arrangement between the fluid coupling halves 110 and 160 can also be referred to as a first partially uncoupled configuration. For example, it can be seen that the projection 164a is approximately in the middle along the slot 114a. In this configuration, the valve of the female coupling 110 is closed, while the valve of the male coupling 160 is still open. In other words, as the fluid coupling halves 110 and 160 are being uncoupled from each other, the valve of the female coupling 110 closes prior to the closing of the male coupling 160. Since the valve of the female coupling 110 is closed, there is no longer an open flow path through the fluid coupling halves 110 and 160.

Figure 8:
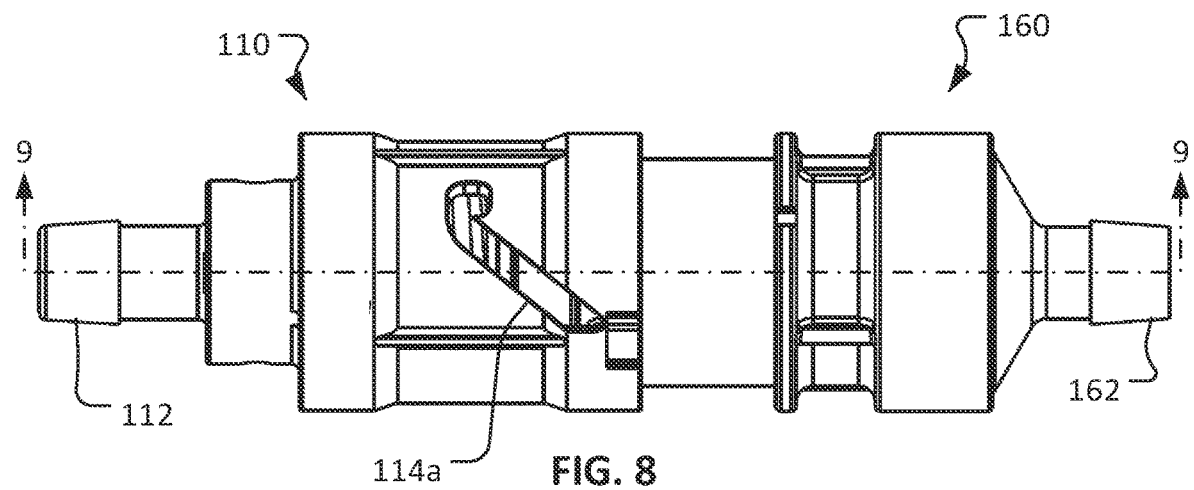
FIG. 8 is a side view of the fluid coupling device of FIG. 1 with the tear-away sleeve removed and configured in a second interim state during disconnection.
Figure 9:
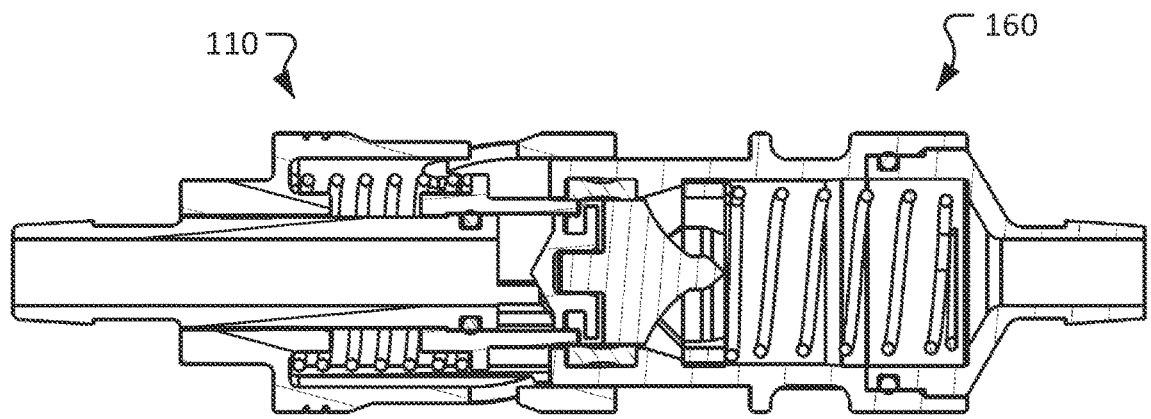
FIG. 9 is a longitudinal cross-sectional view of the fluid coupling device of FIG. 8 taken along the break line 9-9.

FIGS. 8 and 9 depict the fluid coupling halves 110 and 160 in a second state of partial disengagement from each other. This relative arrangement between the fluid coupling halves 110 and 160 can also be referred to as a second partially uncoupled configuration. While not visible, it should be understood that the projections 164a-b are still within the slots 114a-b. Nevertheless, the valve of the male coupling 160 is now closed. Moreover, the valve of the male coupling 160 is mechanically locked in the closed position. Accordingly, the valves of each of the fluid coupling halves 110 and 160 are now closed.

In FIG. 9, it can be seen that the previously open flow path 103 (see FIG. 5) is now fully sealed shut by the valves of the fluid coupling halves 110 and 160. Accordingly, there will be no leakage when the fluid coupling halves 110 and 160 are separated from each other. Moreover, it can also be seen that there are essentially no open regions between the fluid coupling halves 110 and 160 that provide volumetric space for fluid inclusion. Accordingly, there will be essentially no fluid spillage when the fluid coupling halves 110 and 160 are separated from each other.

Figure 11:
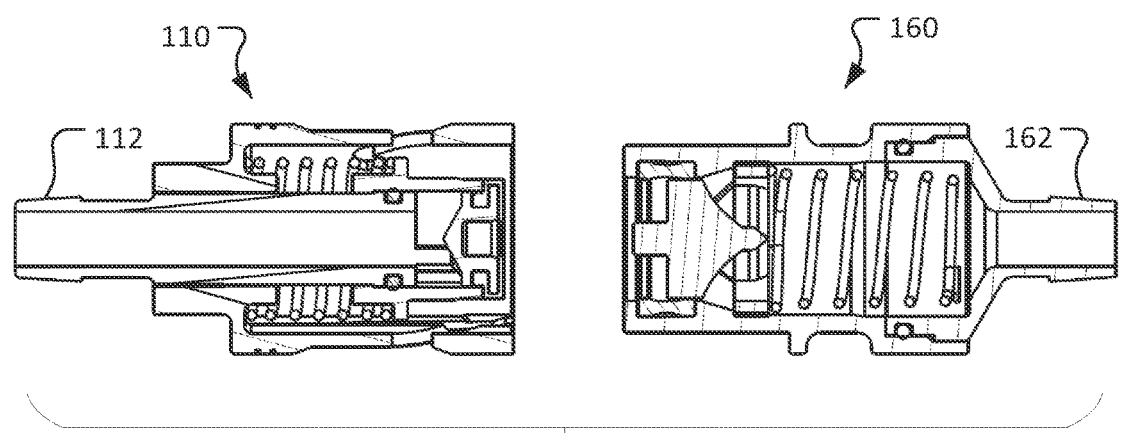
FIG. 11 is a longitudinal cross-sectional view of the fluid coupling device of FIG. 8 taken along the break line 11-11.

FIGS. 10 and 11 depict the fluid coupling halves 110 and 160 fully uncoupled from each other. Once the fluid coupling halves 110 and 160 have been fully uncoupled, they cannot be reconnected to each other because the projections 164a-b are mechanically blocked from being able to re-enter the slots 114a-b, as described further below.

While the fluid coupling halves 110 and 160 are disconnected from each other, fluids are blocked from flowing through the coupling halves 110 and 160 individually. That is, in the disconnected configuration, even if a fluid source is connected to the first connection 112 and/or to the second connection 162, the fluid will not be allowed to flow out of the coupling halves 110 and/or 160. That is the case because, as described further below, a valve member in each of the coupling halves 110 and 160 blocks fluid from flowing out of the coupling halves 110 and 160 while the coupling halves 110 and 160 are disconnected from each other.

Figure 19:
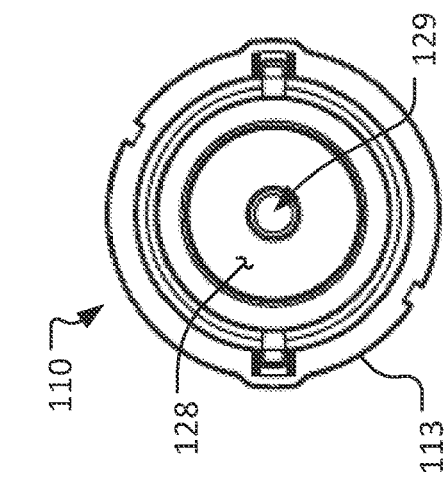
FIG. 19 is an end view of the female coupling portion of FIG. 17.
Figure 17:
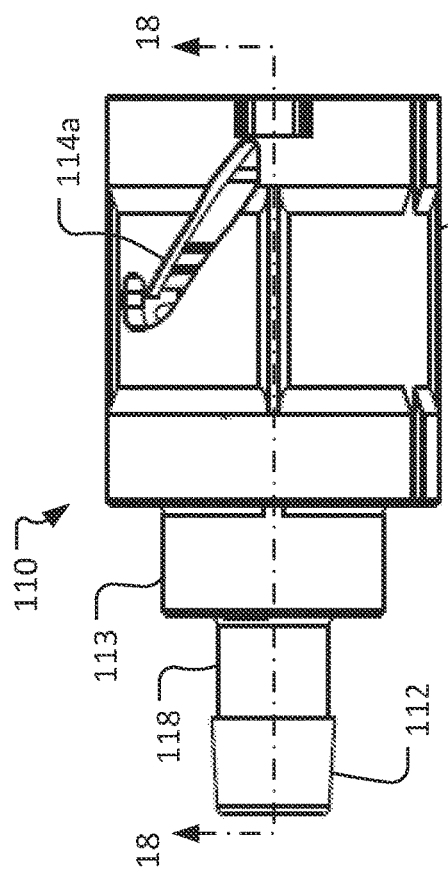
FIG. 17 is a side view of a female coupling portion of the fluid coupling device of FIG. 1.
Figure 18:
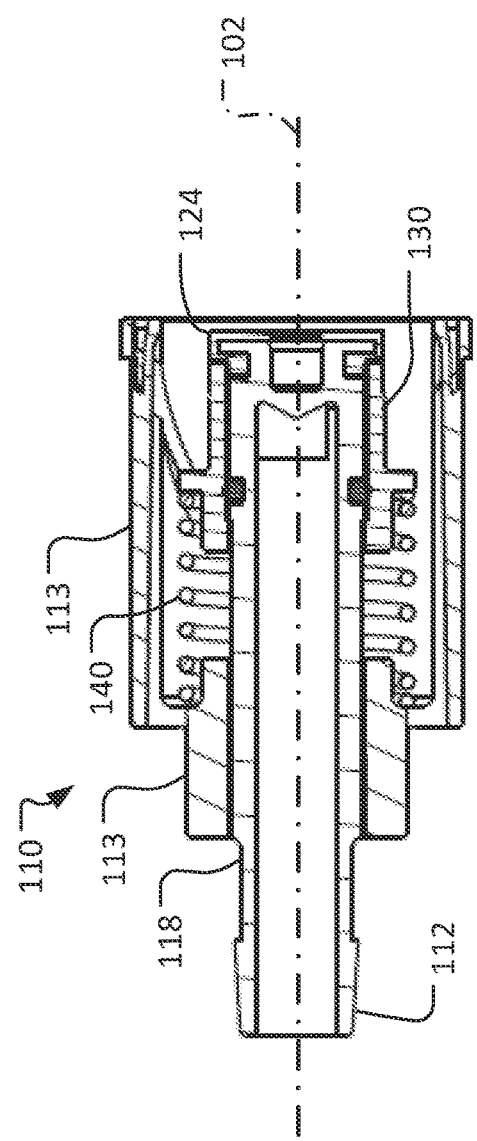
FIG. 18 is a longitudinal cross-sectional view of the female coupling portion of FIG. 17 taken along the break line 18-18.

FIGS. 17-19 show the female coupling 110 in isolation. The female coupling 110 includes a female housing 113, a stem 118 (an end portion of the stem 118 includes the connection 112), a stem gasket 124, a valve sleeve 130, and a spring 140. The female housing 113 defines an internal space and a longitudinal axis 102. The stem 118 extends along the longitudinal axis 102 and is fixedly coupled to the female housing 113. The stem gasket 124 is attached to an end portion of the stem 118 and covers the front surface of the stem 118. The valve sleeve 130 is slidably disposed on the outer diameter of the stem 118. The valve sleeve 130 is movable between an open configuration that allows fluid flow through the stem 118 (e.g., see FIG. 3) and a closed configuration. In the closed configuration (as shown), the valve sleeve 130 shuts off fluid flow through the stem 118 and seals against the stem gasket 124. One end of the spring 140 abuts against the female housing 113 and the opposite end of the spring 140 abuts against the valve sleeve 130. Accordingly, the spring 140 biases the valve sleeve 130 to move toward its closed configuration.

Figure 21:
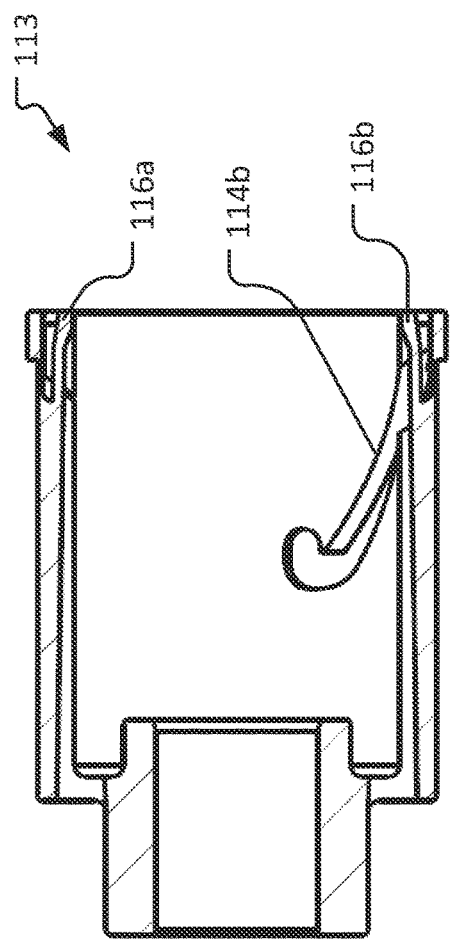
FIG. 21 is a longitudinal cross-sectional view of the housing of FIG. 20 taken along the break line 21-21.
Figure 22:
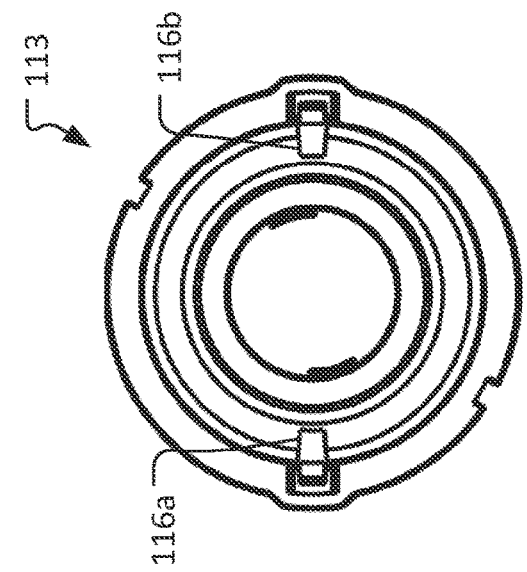
FIG. 22 is an end view of the housing of FIG. 20.
Figure 20:
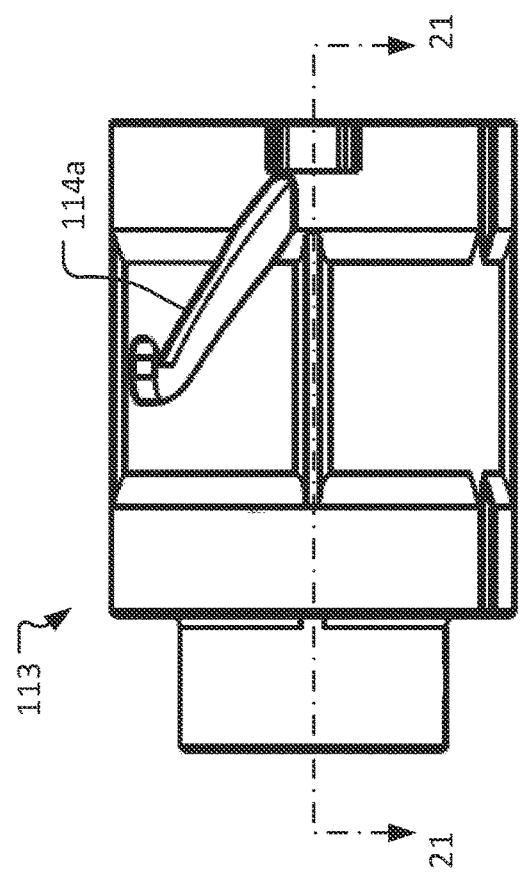
FIG. 20 is a side view of a housing of the female coupling portion of FIG. 17.

FIGS. 20-22 show the female housing 113 in isolation. As described above, the female housing 113 defines the pair of slots 114a-b. At the open outlet end of each of the slots 114a-b is a mechanical blocking member 116a and 116b, respectively. The natural positions of the mechanical blocking members 116a-b are in the open ends of the slots 114a-b so as to block the projections 164a-b of the male coupling 160 (FIGS. 32 and 33) from entering the slots 114a-b at the open ends of the slots 114a-b. Accordingly, after the male coupling 160 has been uncoupled from the female coupling 110 (e.g., as shown in FIGS. 10 and 11), the male coupling 160 cannot be recoupled to the female coupling 110, because of the mechanical blocking members 116a-b. This is one of the features of the fluid coupling device 100 that makes it a single-use, aseptic disconnection fluid coupling device.

The mechanical blocking members 116a-b do not prevent the male coupling 160 from being uncoupled from the female coupling 110 (e.g., as illustrated in FIGS. 6-11) because the mechanical blocking members 116a-b deflect radially outward in reaction to forces exerted by the projections 164a-b of the male coupling 160 as the projections 164a-b pass by the mechanical blocking members 116a-b during their outward travel along the slots 114a-b during uncoupling.

Figure 24:
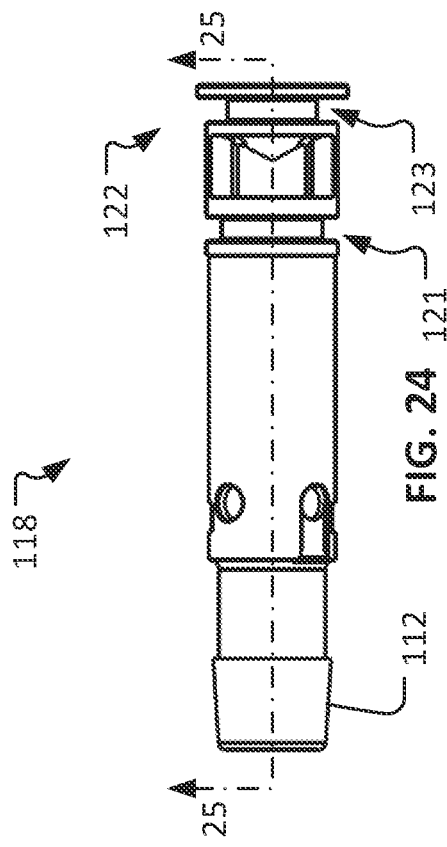
FIG. 24 is a side view of the stem of FIG. 23.
Figure 25:
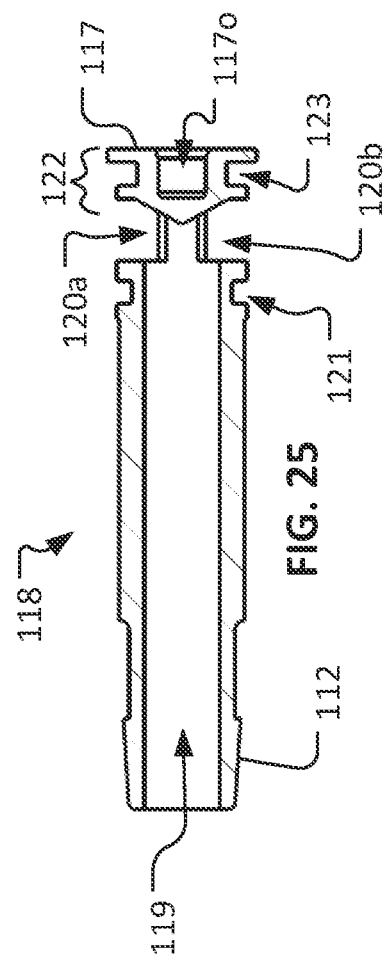
FIG. 25 is a longitudinal cross-sectional view of the stem of FIG. 24 taken along the break line 25-25.
Figure 23:
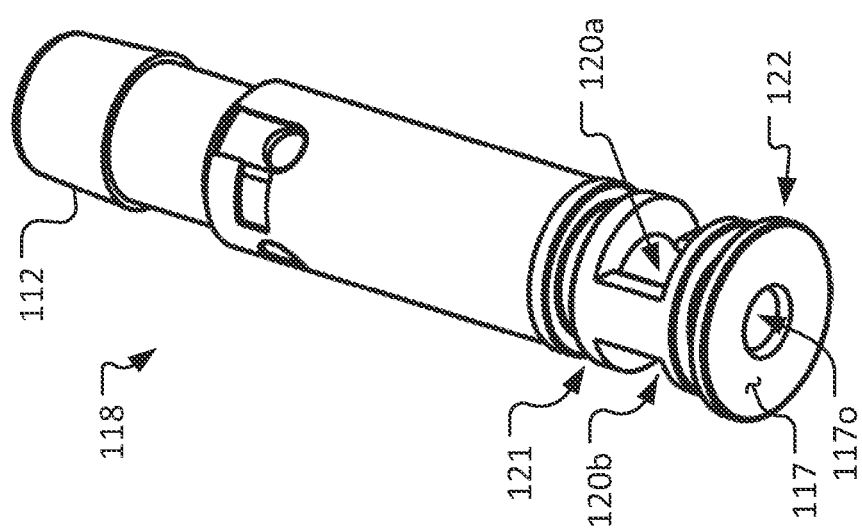
FIG. 23 is a perspective view of a stem component of the female coupling portion of FIG. 17.

FIGS. 23-25 show the stem 118 in isolation. The stem 118 defines a longitudinally extending bore 119 (which comprises a portion of the fluid flow path). The stem 118 also defines a first lateral opening 120a and a second lateral opening 120b that are in fluid communication with the bore 119. The fluid flow path passes through the lateral openings 120a-b while the valve sleeve 130 is in the open configuration (e.g., as shown in FIGS. 3 and 5). However, when the valve sleeve 130 is in the closed configuration (e.g., as shown in FIGS. 7, 9, and 11) the valve sleeve 130 fully occludes the lateral openings 120a-b so that no fluid can flow through the lateral openings 120a-b.

The stem 118 defines an annular groove 121 in its outer diameter. The annular groove 121 can contain a seal (e.g., an elastomeric ring) that can contact the inner diameter of the valve sleeve 130.

The stem 118 also includes an end portion 122 (which is on the opposite end of the stem 118 in comparison to the connection 112). The end portion 122 is configured to receive the stem gasket 124 (which is an elastomeric seal member). The end portion 122 defines an annular groove 123 and a front face surface 117. The front face surface 117 faces the male coupling valve member while the male coupling 160 and the female coupling 110 are coupled together. In the depicted embodiment, the front face surface 117 is planar and it defines a central opening 117o to a recess. The stem gasket 124 is disposed on the front face surface 117 of the stem 118 (e.g., as shown in FIG. 18, etc.) so as to abut the valve member of the male coupling 160 (e.g., as shown in FIGS. 3, 5, 7, and 9).

FIGS. 26-28 show the stem gasket 124 in isolation. The stem gasket 124 can be made of materials such as, but not limited to, silicone, fluoroelastomers (FKM), ethylene propylene diene monomer (EPDM), thermoplastic elastomers (TPE), buna, buna-N, thermoplastic vulcanizates (TPV), and the like.

The stem gasket 124 provides multiple sealing areas, surfaces, or regions that other components of the fluid coupling halves 110 and 160 seal against. For example, the stem gasket 124 includes a first sealing area 125 that the inner diameter of the valve sleeve 130 seals against when the valve sleeve 130 is in the closed position (e.g., as shown in FIGS. 7, 9, and 11). The stem gasket 124 also includes a second sealing area 126 that the annular end of the valve sleeve 130 seals against when the valve sleeve 130 is in the closed position (e.g., as shown in FIGS. 7, 9, and 11). The stem gasket 124 also includes a third sealing area 127 that components of the male coupling 160 seal against during the process of uncoupling the male coupling 160 and the female coupling 110. The stem gasket 124 also includes a fourth sealing area 128 that the valve member of the male coupling 160 seals against while the male coupling 160 and the female coupling 110 are coupled together (e.g., as shown in FIGS. 3, 5, 7, and 9).

The stem gasket 124 also defines a central opening 129 in the fourth sealing area 128 that seals against the valve member of the male coupling 160. The central opening 129 aligns with the central opening 117*o* and recess of the stem 118.

While in the depicted embodiment the fourth sealing area 128 that the valve member of the male coupling 160 seals against while the male coupling 160 and the female coupling 110 are coupled together (e.g., as shown in FIGS. 3, 5, 7, and 9) is attached to the stem 118, in some embodiments the seal between the valve member of the male coupling 160 and the female coupling 110 can instead be attached to the valve member of the male coupling 160.

Figure 30:
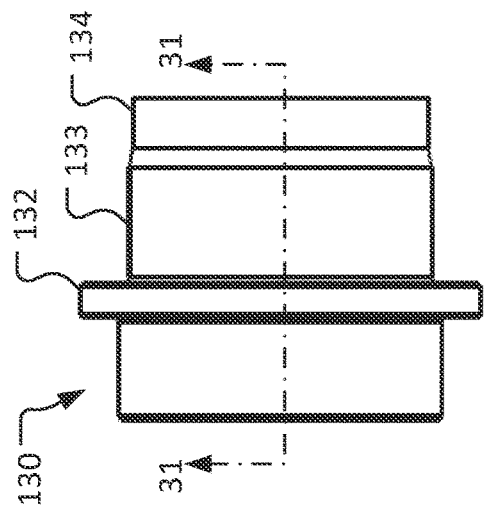
FIG. 30 is a side vice of the sleeve of FIG. 29.
Figure 31:
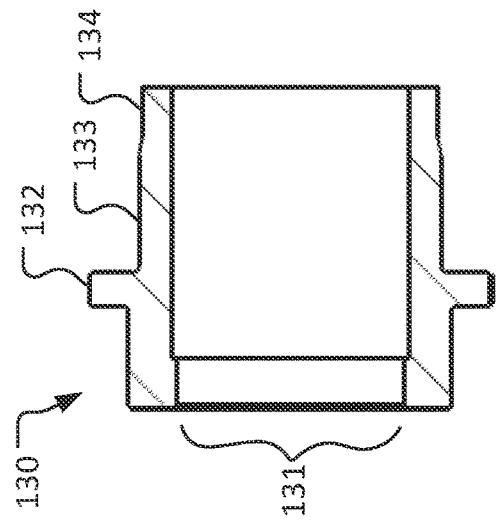
FIG. 31 is a longitudinal cross-sectional view of the sleeve of FIG. 29 taken along the break line 31-31.
Figure 29:
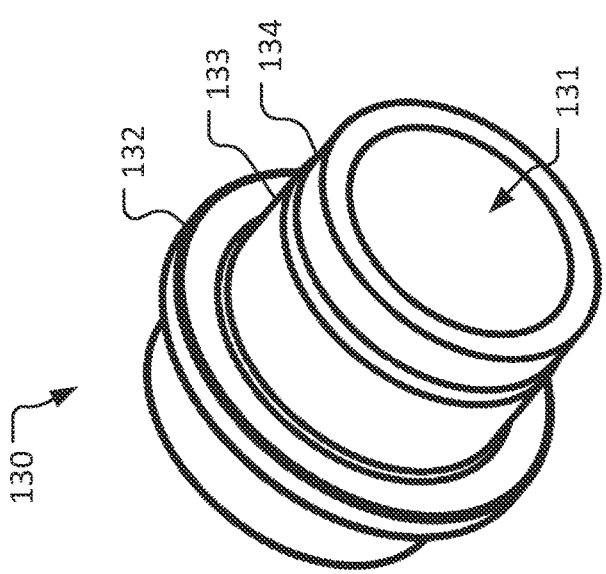
FIG. 29 is perspective view of a sleeve component of the female coupling portion of FIG. 17.

FIGS. 29-31 show the valve sleeve 130 in isolation. The valve sleeve 130 defines a bore 131 that slidably receives the stem 118. That is, the valve sleeve 130 slides along the stem 118 as the valve sleeve 130 moves between its open and closed positions.

The valve sleeve 130 includes an annular projection 132. The spring 140 of the female coupling 110 pushes against the annular projection 132 to bias the valve sleeve 130 toward the closed position. The opposite side of the annular projection 132 (i.e., opposite of the side of the annular projection 132 that is in contact with the spring 140) is abutted by the housing of the male coupling 160 when the male coupling 160 and the female coupling 110 are coupled together (e.g., as shown in FIGS. 3, 5, and 7). By virtue of the abutment between the housing of the male coupling 160 and the annular projection 132, the valve sleeve 130 is maintained in its open position while the male coupling 160 and the female coupling 110 are fully coupled together.

The valve sleeve 130 also includes a first cylindrical sealing surface portion 133 and a second cylindrical sealing surface portion 134. The second cylindrical sealing surface portion 134 is smaller in diameter than the first cylindrical sealing surface portion 133. As shown in FIGS. 3, 5, and 7, the first and second cylindrical sealing portions 133 and 134 both seal against the inner diameter of a male gasket 180 (the male gasket is shown e.g., in FIGS. 39-41) while the fluid coupling device 100 is in the fully coupled configuration (FIGS. 3 and 5) and in the first partially uncoupled configuration (FIG. 7). When the fluid coupling device 100 is in the second partially uncoupled configuration (FIG. 9), only the second cylindrical sealing portion 134 (not the first cylindrical sealing surface 133) abuts and seals against the inner diameter of the male gasket 180.

Figure 33:
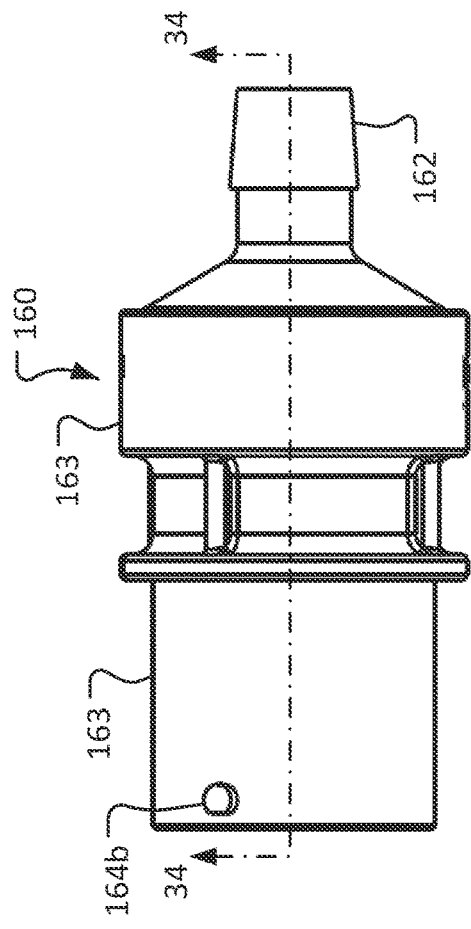
FIG. 33 is a side view of the male coupling portion of FIG. 32.
Figure 34:
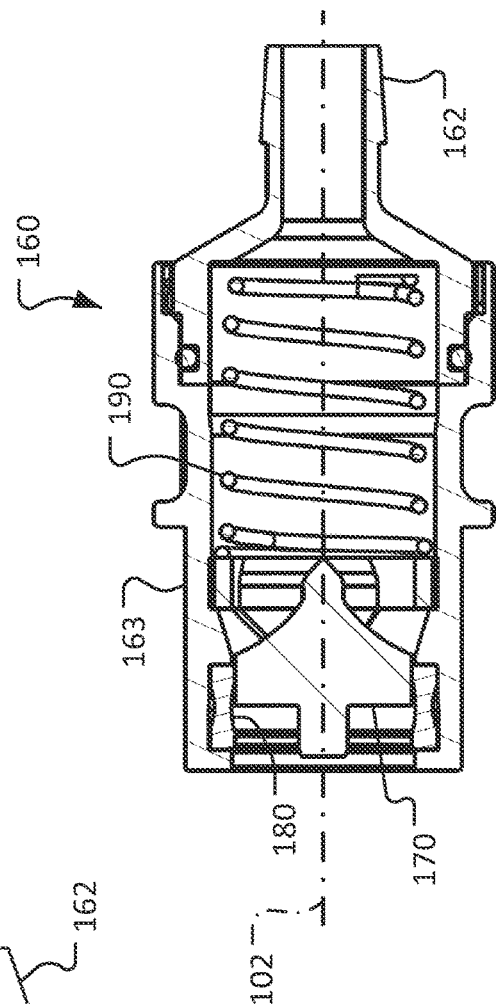
FIG. 34 is a longitudinal cross-sectional view of the male coupling portion of FIG. 33 taken along the break line 34-34.
Figure 32:
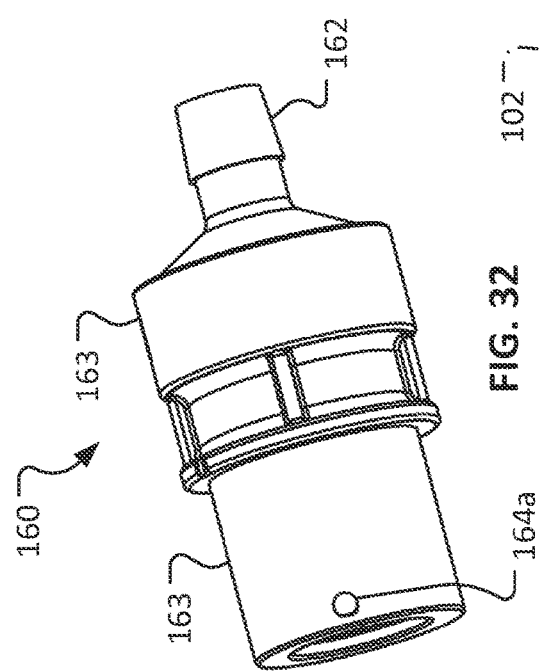
FIG. 32 is a perspective view of a male coupling portion of the fluid coupling device of FIG. 1.

FIGS. 32-34 show the male coupling 160 in isolation. The male coupling 160 includes a male housing 163, a male valve member 170, a male gasket 180, and a spring 190. The male housing 163 defines an internal space and a longitudinal axis 102. The male valve member 170 and the spring 190 are disposed within the internal space defined by the male housing 163. The spring 190 bears against the male valve member 170 to bias the male valve member 170 to move toward its closed position. When the fluid coupling device 100 is in the fully coupled configuration the spring 190 is compressed between the male valve member and the male housing 163.

The male valve member 170 (which is shown in its closed position in FIG. 34) slidably moves, relative to the male housing 163, along the longitudinal axis 102 from its open position toward its closed position as the fluid coupling device 100 is transitioned from the fully coupled configuration to its uncoupled configurations (as shown in FIGS. 3, 5, 7, 9, and 11). More specifically, the male valve member 170 is in its open position while the fluid coupling device 100 is in the fully coupled configuration (e.g., as shown in FIGS. 3 and 5) and while the fluid coupling device 100 is in the first partially uncoupled configuration (as shown in FIG. 7). However, the male valve member 170 is in its closed position while the fluid coupling device 100 is in the second partially uncoupled configuration (as shown in FIG. 9) and while the male coupling 160 is fully uncoupled from the female coupling 110 (as shown in FIGS. 11 and 34).

FIGS. 35-38 show the male valve member 170 in isolation. The male valve member 170 includes a base 172, ribs 174, a core 176, and a projection 178. The ribs 174 extend between the base 172 and the core 176. One or more openings are defined between the ribs 174. The open flow path 103 (as shown in FIG. 3) extends through the one or more openings defined between the ribs 174 of the male valve member 170.

The projection 178 extends from the front face of the core 176. While the female coupling 110 and the male coupling 160 are coupled, the projection 178 extends through the central opening 129 of the stem gasket 124 and through the central opening 117*o* defined by the front face surface 117 of the end portion 122 of the stem 118, and into the recess defined by the end portion 122 of the stem 118. The leading end portion of the projection 178 is chamfered.

The spring 190 presses against the base 172 to bias the male valve member 170 toward its closed position. The base 172 includes a first latch member 173*a* and a second latch member 173*b*. The latch members 173*a-b* can extend radially outward from the base 172 so as to engage with the male housing 163 when the male valve member 170 is in its closed position (e.g., as shown in FIGS. 9, 11, and 34). The latching effect of the latch members 173*a-b* relative to the male housing 163 causes the male valve member 170 to be detained in its closed position. That is, when the male valve member 170 moves to its closed position, the male valve member 170 is permanently detained, or locked, in the closed position. This latching of the male valve member 170 is one of the features of the fluid coupling device 100 that makes it a single-use, aseptic disconnection fluid coupling device.

The core 176 has a conical surface 171, a cylindrical surface 175, and a front face 177. The conical surface 171 is shaped to minimize the resistance to fluid flow through the male valve member 170. The cylindrical surface 175 seals against the inner diameter of the male gasket 180 (e.g., as shown in FIGS. 9, 11, and 34) while the male valve member 170 is in the closed position. The front face 177 is planar and circular. The front face 177 abuts and seals against the fourth sealing area 128 of the stem gasket 124.

FIGS. 39-41 show the male gasket 180 in isolation. The male gasket 180 is positioned in an annular recess defined by the inner diameter of the male housing 163. The male gasket 180 can be made of materials such as, but not limited to, silicone, fluoroelastomers (FKM), ethylene propylene diene monomer (EPDM), thermoplastic elastomers (TPE), buna, buna-N, thermoplastic vulcanizates (TPV), and the like. The male gasket 180 can have a variety of cross-sectional shapes. In the depicted embodiment, the male gasket 180 has an hour-glass cross-sectional shape.

The inner diameter of the male gasket 180 abuts and seals against the first and second cylindrical sealing portions 133 and 134 of the valve sleeve 130 while the valve sleeve 130 is in its open position (e.g., as shown in FIGS. 3 and 5), and while the fluid coupling device 100 is in the first partially uncoupled configuration (FIG. 7). When the fluid coupling device 100 is in the second partially uncoupled configuration (FIG. 9), the second cylindrical sealing portion 134 (not the first cylindrical sealing surface 133) abuts and seals against the inner diameter of the male gasket 180, and the cylindrical surface 175 of the male valve member 170 abuts and seals against the inner diameter of the male gasket 180. When the female coupling 110 is fully uncoupled from the male coupling 160, only the cylindrical surface 175 of the male valve member 170 abuts and seals against the inner diameter of the male gasket 180.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A single-use aseptic fluid coupling device, comprising:
   a male coupling comprising:
      a male housing defining an internal space and a longitudinal axis; and
      a male coupling valve member within the internal space and slidable relative to the male housing along the longitudinal axis of the male housing from an open position to a closed position;
   a female coupling releasably coupled to the male coupling component and comprising:
      a female housing defining an internal space and a longitudinal axis; and
      a stem fixedly coupled to the female housing and extending along the longitudinal axis of the female housing, the stem having a front surface facing the male coupling valve member, the stem defining an open bore extending longitudinally and one or more lateral openings fluidly coupling the open bore and the internal space of the male housing such that an open flow path extends through the female coupling and the male coupling while they are releasably coupled to each other;
      an elastomeric seal disposed on the front surface of the stem such that the male coupling valve member is abutting the elastomeric seal; and
   a tear-away sleeve coupled to the male and female couplings while the male and female couplings are releasably coupled to each other.

2. The single-use aseptic fluid coupling device of claim 1, wherein the front surface of the stem is planar.

3. The single-use aseptic fluid coupling device of claim 2, wherein the front surface of the stem defines an opening.

4. The single-use aseptic fluid coupling device of claim 3, wherein the male coupling valve member includes a projection that extends through the elastomeric seal and into the opening.

5. The single-use aseptic fluid coupling device of claim 1, wherein a spring in the internal space of the male housing moves the male coupling valve member to the closed position in response to uncoupling the male and female couplings from each other.

6. The single-use aseptic fluid coupling device of claim 5, wherein the male coupling valve member locks in the closed position in response to moving to the closed position.

7. The single-use aseptic fluid coupling device of claim 1, wherein the tear-away sleeve prevents uncoupling of the male and female couplings while the tear-away sleeve is coupled to the male and female couplings.

8. The single-use aseptic fluid coupling device of claim 1, wherein, in order to uncouple the male and female couplings from each other, the tear-away sleeve must be destructively removed from being coupled to the male and female couplings.

9. The single-use aseptic fluid coupling device of claim 1, wherein the male and female couplings can be uncoupled from each other by simultaneously rotating and translating the male coupling relative to the female coupling.

10. The single-use aseptic fluid coupling device of claim 1, wherein, after the male and female couplings have been uncoupled from each other, latches are activated that block and prevent the male and female couplings from being coupled together again.

11. A single-use aseptic fluid coupling device, comprising:
   a male coupling comprising:
      a male housing defining an internal space and a longitudinal axis; and
      a male coupling valve member within the internal space and slidable relative to the male housing along the longitudinal axis of the male housing from an open position to a closed position; and
   a female coupling releasably coupled to the male coupling component and comprising:
      a female housing defining an internal space and a longitudinal axis; and
      a stem fixedly coupled to the female housing and extending along the longitudinal axis of the female housing, the stem having a front surface facing the male coupling valve member, the stem defining an open bore extending longitudinally and one or more lateral openings fluidly coupling the open bore and the internal space of the male housing such that an open flow path extends through the female coupling and the male coupling while they are releasably coupled to each other,
      an elastomeric seal disposed on the front surface of the stem such that the male coupling valve member is abutting the elastomeric seal, wherein, after the male and female couplings have been uncoupled from each other, latches are activated that block and prevent the male and female couplings from being coupled together again.

12. The single-use aseptic fluid coupling device of claim 11, wherein the front surface of the stem is planar.

13. The single-use aseptic fluid coupling device of claim 12, wherein the front surface of the stem defines an opening.

14. The single-use aseptic fluid coupling device of claim 13, wherein the male coupling valve member includes a projection that extends through the elastomeric seal and into the opening.

15. The single-use aseptic fluid coupling device of claim 11, wherein a spring in the internal space of the male housing moves the male coupling valve member to the closed position in response to uncoupling the male and female couplings from each other.

16. The single-use aseptic fluid coupling device of claim 15, wherein the male coupling valve member locks in the closed position in response to moving to the closed position.

17. The single-use aseptic fluid coupling device of claim 11, further comprising a tear-away sleeve coupled to the male and female couplings while the male and female couplings are releasably coupled to each other.

18. The single-use aseptic fluid coupling device of claim 17, wherein the tear-away sleeve prevents uncoupling of the male and female couplings while the tear-away sleeve is coupled to the male and female couplings.

19. The single-use aseptic fluid coupling device of claim 17, wherein, in order to uncouple the male and female couplings from each other, the tear-away sleeve must be destructively removed from being coupled to the male and female couplings.

20. The single-use aseptic fluid coupling device of claim 11, wherein the male and female couplings can be uncoupled from each other by simultaneously rotating and translating the male coupling relative to the female coupling.

* * * * *

UNITED STATES PATENT AND TRADEMARK OFFICE
CERTIFICATE OF CORRECTION

PATENT NO. : 11,566,736 B2  
APPLICATION NO. : 17/138020  
DATED : January 31, 2023  
INVENTOR(S) : Loi T. Truong Page 1 of 1

It is certified that error appears in the above-identified patent and that said Letters Patent is hereby corrected as shown below:

On the Title Page

Item (71), Applicant, Line 2: Delete "CA" and insert -- MN --.

Signed and Sealed this
Fifteenth Day of August, 2023

Katherine Kelly Vidal
*Director of the United States Patent and Trademark Office*